United States Patent
Kumar et al.

(10) Patent No.: US 11,241,379 B2
(45) Date of Patent: Feb. 8, 2022

(54) PARENTERAL DOSAGE FORM OF DILTIAZEM

(71) Applicant: SUN PHARMACEUTICAL INDUSTRIES LTD., Mumbai (IN)

(72) Inventors: Samarth Kumar, Baroda (IN); Milan Natvarbhai Thakkar, Baroda (IN); Kandarp Maheshkumar Dave, Baroda (IN)

(73) Assignee: SUN PHARMACEUTICAL INDUSTRIES LIMITED, Maharashtra (IN)

( * ) Notice: Subject to any disclaimer, the term of this patent is extended or adjusted under 35 U.S.C. 154(b) by 430 days.

(21) Appl. No.: 15/780,793

(22) PCT Filed: Dec. 1, 2016

(86) PCT No.: PCT/IN2016/050429
§ 371 (c)(1),
(2) Date: Jun. 1, 2018

(87) PCT Pub. No.: WO2017/094029
PCT Pub. Date: Jun. 8, 2017

(65) Prior Publication Data
US 2020/0246254 A1    Aug. 6, 2020

(30) Foreign Application Priority Data

Dec. 1, 2015   (IN) .......................... 4533/MUM/2015

(51) Int. Cl.
*A61K 9/00* (2006.01)
*A61J 1/10* (2006.01)
*A61K 31/554* (2006.01)
*A61K 47/10* (2017.01)

(52) U.S. Cl.
CPC .............. *A61K 9/0019* (2013.01); *A61J 1/10* (2013.01); *A61K 31/554* (2013.01); *A61K 47/10* (2013.01)

(58) Field of Classification Search
None
See application file for complete search history.

(56) References Cited

U.S. PATENT DOCUMENTS

| 7,490,639 | B2 | 2/2009 | Py |
| 7,992,597 | B2 | 8/2011 | Py et al. |
| 2004/0265238 | A1 | 12/2004 | Chaudry |
| 2011/0009836 | A1* | 1/2011 | Chebli ................. A61F 9/0008 |
| | | | 604/298 |
| 2013/0333796 | A1 | 12/2013 | Py |

FOREIGN PATENT DOCUMENTS

| CN | 1600314 A | 3/2005 |
| CN | 100427095 | * 10/2008 |
| CN | 102240262 A | 11/2011 |
| JP | H288527 | 11/2012 |
| KR | 840002819 A | 7/1984 |
| KR | 860002034 B1 | 7/1984 |

OTHER PUBLICATIONS

CN102240262 Machine Translation, Obtained from EPO, Nov. 2011 (Year: 2011).*
Sigma Aldrich Ethanol, Prodcut Comparison Guide, retrieved online on Jul. 22, 2020 (Year: 2020).*
International Application No. PCT/IN2016/050429, International Preliminary Report dated Jun. 5, 2018, pp. 1-5.
International Application No. PCT/IN2016/050429, International Search Report and Written Opinion dated Apr. 4, 2017 pp. 7.
Japanese Application No. 2018-528283, Office Action dated Sep. 8, 2020, 2 pages.
Commentary to the 13th Edition of the Japanese Pharmacopoeia, Part 1: Pharmaceutical Articles, ("A" Column) to ("Sa" Column), C-596-C-600, Feb. 19, 1999, 8 pgs.
Kurt H. Bauer, "Solubilization of Drugs Using Organic Solvents, Micellar Solutions, or Other Colloidal Dispersions," The Practice of Medicinal Chemistry, vol. 2, p. 393-409, Sep. 25, 1999.

* cited by examiner

*Primary Examiner* — Jennifer A Berrios
(74) *Attorney, Agent, or Firm* — Blank Rome LLP

(57) ABSTRACT

The present invention relates to a parenteral dosage form comprising a) a ready-to-infuse, stable aqueous solution comprising diltiazem or its pharmaceutically acceptable salt, pH adjusting agent to provide a pH in the range of 3 to 5 and ethanol, and b) an infusion container filled with said aqueous solution.

13 Claims, 2 Drawing Sheets

PARENTERAL DOSAGE FORM OF DILTIAZEM

FIELD OF THE INVENTION

The present invention relates to a parenteral dosage form of diltiazem comprising a ready-to-infuse, stable aqueous solution of diltiazem in an infusion container.

BACKGROUND OF THE INVENTION

Diltiazem is a calcium ion influx inhibitor (slow channel blocker or calcium channel antagonist). Chemically, diltiazem hydrochloride is 1,5-benzothiazepin-4(5H)one,3-(acetyloxy)-5-[2-(dimethylamino)ethyl]-2, 3-dihydro-2-(4-methoxy phenyl)-, monohydro-chloride, (+)-cis- and has the following structural formula:

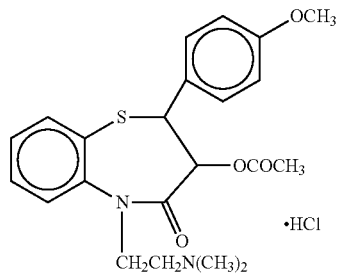

Diltiazem, inhibits the influx of calcium (Ca) ions during membrane depolarization of cardiac and vascular smooth muscle. Diltiazem hydrochloride is administered by intravenous infusion for temporary control of rapid ventricular rate in atrial fibrillation or atrial flutter and rapid conversion of paroxysmal supraventricular tachycardias (PSVT) to sinus rhythm. The commercially available injectable products of diltiazem are pre-concentrate solutions which need to be diluted with a suitable diluent like dextrose or sodium chloride solution before use. One such product by Bedford® is a diltiazem hydrochloride 5 mg/ml injection solution, supplied in 5 ml and 10 ml vials. The step of dilution and handling involves risk of potential calculation or dilution error as well as risk of microbiological contamination during handling. Further, diltiazem is known to be susceptible to hydrolysis and degradation in aqueous solutions. The degradation is undesirable as it results in loss of titer of the active ingredient, and leads to formation of impurities or related compounds which have negligible activity and are undesirable. The major pathway of degradation is o-deacetylation which leads to formation of impurity 'desacetyl diltiazem'.

Thus, there is a need in the art for a stable parenteral dosage form of diltiazem, which comprise an aqueous solution of diltiazem that is ready-to-infuse without manipulation, i.e. in the pre-diluted form that can be directly infused or injected thus eliminating the risk of any potential calculation or dilution error as well as risk of microbiological contamination during handling and at the same time is stable for prolonged period of time. The present invention fulfills this need.

The inventors have found a parenteral dosage form comprising a) a ready-to-infuse, stable aqueous solution comprising diltiazem or its pharmaceutically acceptable salt, pH adjusting agent to provide a pH in the range of 3 to 5 and ethanol, and b) an infusion container filled with said aqueous solution.

It was a surprising finding of the present inventors that presence of ethanol stabilizes diltiazem in aqueous solution and protects it from degradation, while other alcoholic co-solvents enhances the degradation of diltiazem in aqueous solution.

SUMMARY OF THE INVENTION

The present invention provides a parenteral dosage form comprising
  a. a ready-to-infuse, stable aqueous solution comprising diltiazem or its pharmaceutically acceptable salt, pH adjusting agent to provide a pH in the range of 3 to 5 and ethanol, and
  b. an infusion container filled with said aqueous solution.

DESCRIPTION OF THE INVENTION

Figure 1:
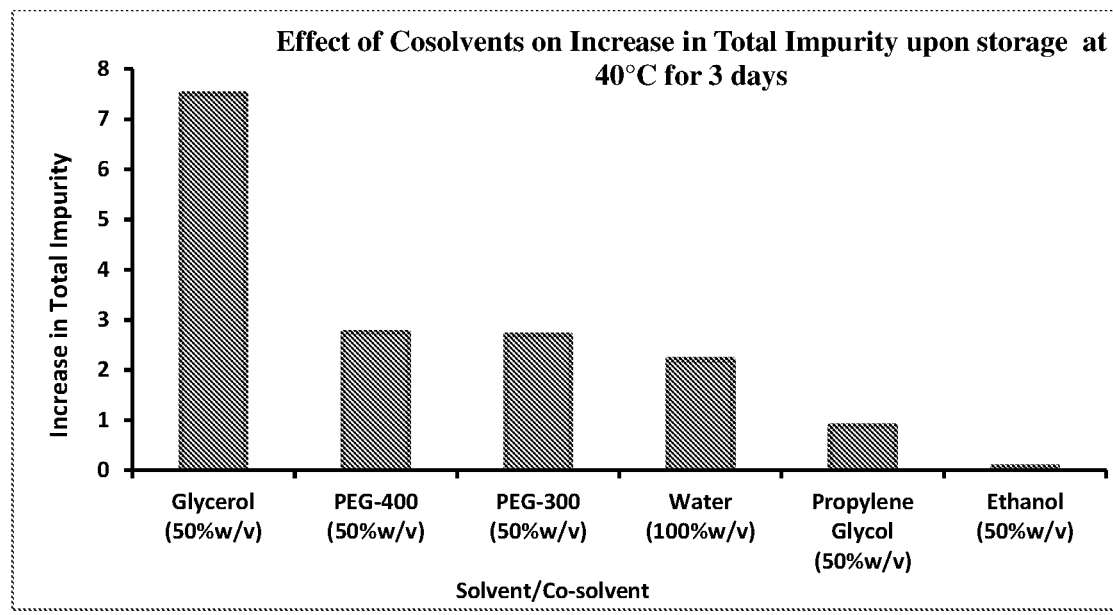
FIG. 1: It gives a graph depicting the effect of co-solvents on the increase in the total impurity when the parenteral dosage form is stored at 40° C. for 3 days. For the comparative examples, the parenteral dosage form is prepared as per comparative examples A to E and the parenteral dosage form of the present invention, is prepared as described in Example (V).
Figure 2:
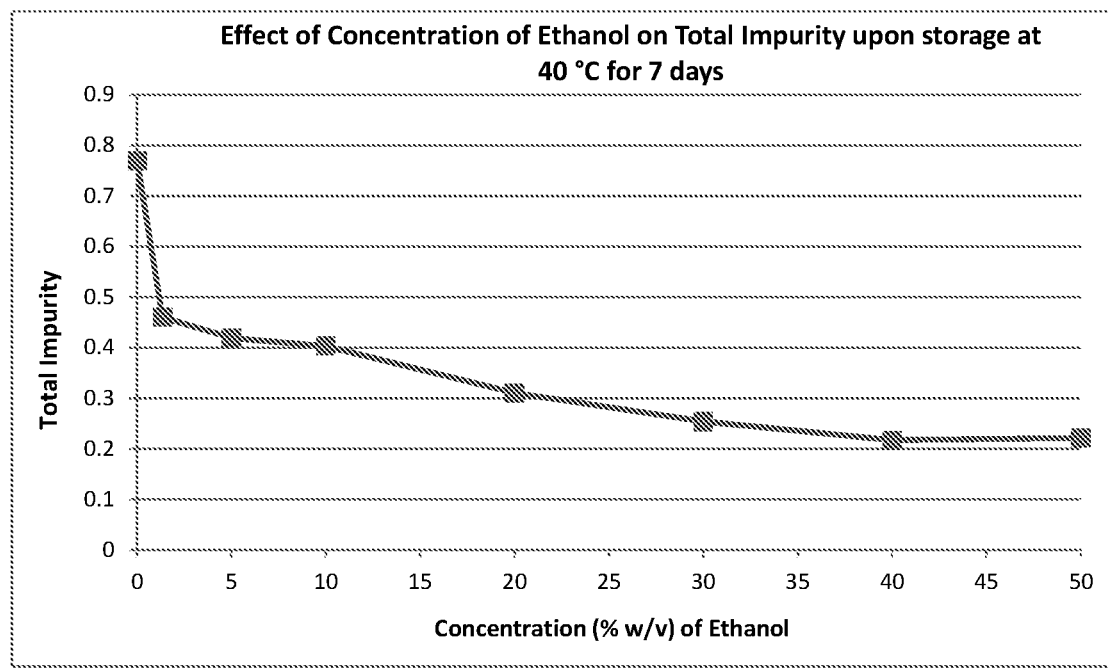
FIG. 2: It gives a graph depicting the effect of concentration of ethanol on the total impurity level (increase from initial) when the parenteral dosage form is stored at 40° C. for 7 days. It is evident that when the concentration of ethanol is increased, it results in a more stable aqueous solution with lesser amount of total impurities.

The term diltiazem, as used herein covers diltiazem as well as its pharmaceutically acceptable salts thereof, such as diltiazem hydrochloride.

The term 'ready-to-infuse' as used herein means that the aqueous drug solution is sterile and suitable for direct intravenous infusion or injection without manipulation, that is, no intermediate steps of dilution or reconstitution are required before administration or infusion of the drug solution to the patient. The aqueous drug solution can be directly administered parenterally from the container of the dosage form. The term "ready-to-infuse" is synonymous with "ready-to-inject" or "ready-to-administer". The ready-to-infuse parenteral dosage form according to the present invention avoids the inconvenience of reconstituting or diluting a lyophilized or concentrated parenteral formulation into infusion diluents prior to infusion, as well as eliminates the risk of any potential calculation or dilution error as well as risk of microbiological contamination during handling. The present invention provides stable parenteral dosage form of diltiazem having a ready-to-infuse aqueous solution of diltiazem and it does not relate to semi-solid topical dosage forms (such as gel, hydrogel, emulgel, paste, cream, ointment etc.) and/or non-aqueous dosage forms that are not suitable for parenteral administration.

The parenteral dosage form of the present invention is 'stable'. As used herein, the term 'stable' means that the dosage form of the present invention is physically as well as chemically stable upon storage for prolonged period of time such as for at least 6 months, preferably 12 months, more preferably for 24 months when stored at 2-8° C. and/or for a period of 6 months when stored at 25° C. (accelerated stability condition). When stored at these conditions, the aqueous solution of diltiazem or its pharmaceutically acceptable salt remains chemically stable such that the assay of diltiazem remains within 90-110% by weight of the label claim, the content of total impurities remain within 0-5 w/w of diltiazem hydrochloride and the content of impurity 'desacetyl diltiazem' remain within 0-5% by weight of diltiazem hydrochloride. The impurities are expressed as % by weight of diltiazem hydrochloride.

The present invention provides a parenteral dosage form comprising a) a ready-to-infuse, stable aqueous solution comprising diltiazem or its pharmaceutically acceptable salt, pH adjusting agent to provide a pH in the range of 3 to 5 and ethanol, and b) an infusion container filled with said aqueous solution.

The present invention provides a parenteral dosage form comprising (a) a ready-to-infuse, stable aqueous solution consisting essentially of diltiazem or its pharmaceutically acceptable salt, pH adjusting agent to provide a pH in the range of 3 to 5 and ethanol, and b) an infusion container filled with said aqueous solution. This means that the aqueous solution is free of alcoholic co-solvent other than ethanol.

The present invention provides a parenteral dosage form comprising a) a ready-to-infuse, stable aqueous solution consisting of diltiazem or its pharmaceutically acceptable salt, pH adjusting agent to provide a pH in the range of 3 to 5 and ethanol, and b) an infusion container filled with said aqueous solution.

The aqueous solution filled into the infusion container of the dosage form comprises diltiazem or its pharmaceutically acceptable salt as the sole active ingredient. In one preferred embodiment, the hydrochloride salt of diltiazem is employed. Diltiazem or its pharmaceutically acceptable salt is present in the aqueous solution of the present invention at a concentration which allows direct infusion of the aqueous solution to the patient without the need of further dilution. It may be present at a concentration ranging from about 0.05 mg/ml to about 2.0 mg/ml, preferably from about 0.1 mg/ml to about 2.0 mg/ml, such as for example 0.2, 0.3, 0.4, 0.5, 0.6, 0.7, 0.8, 0.9, 1.0, 1.1, 1.2, 1.3, 1.4, 1.5, 1.6, 1.7, 1.8 or 1.9 mg/ml, more preferably from about 0.4 mg/ml to about 1.0 mg/ml. In one particular embodiment, diltiazem hydrochloride is present in the aqueous solution in an amount of 1.0 mg/ml. In another particular embodiment, diltiazem hydrochloride is present in the aqueous solution in an amount of 0.83 mg/ml. In another particularly preferred embodiment, diltiazem hydrochloride is present in the aqueous solution in an amount of 0.45 mg/ml. The parenteral dosage form of the present invention includes the aqueous solution of diltiazem filled into infusion container which may be rigid or flexible in nature. The volume capacity of each unit of the container may range from about 50 ml to about 500 ml. The aqueous solution may present in the infusion containers in volumes ranging from about 50 ml to 500 ml per infusion container, such as for example 50 ml, 75 ml, 100 ml, 120 ml, 125 ml, 140 ml, 150 ml, 160 ml, 175 ml, 180 ml, 190 ml, 200 ml, 220 ml, 225 ml, 240 ml, 250 ml, 260 ml, 275 ml, 280 ml, 290 ml, 300 ml, 320 ml, 325 ml, 340 ml, 350 ml, 360 ml, 375 ml, 380 ml, 390 ml, 400 ml, 420 ml, 425 ml, 430 ml, 440 ml, 450 ml, 460 ml, 470 ml, 475 ml, 480 ml, 490 ml or 500 ml. According to preferred embodiments of the present invention, the ready-to-infuse parenteral dosage form provides large volume containers such as infusion bags, which can accommodate a volume of at least 50 ml, preferably from about 100 ml to 500 ml of the aqueous solution.

Ethanol is present in the aqueous solution of the present invention in an amount ranging from about 1.0% w/v to about 50% w/v, preferably from about 1.0% w/v to about 20.0% w/v, more preferably from about 1.0% w/v to about 10.0% w/v, such as for example 1.5, 2.0, 2.5, 3.0, 3.5, 4.0, 4.5, 5.0, 5.5, 6.0, 6.5, 7.0, 7.5, 8.0, 8.5, 9.0 or 9.5% w/v, more preferably from about 5.0% to 10.0% w/v. In one particularly preferred embodiment, the ethanol is present in the ready-to-infuse aqueous solution in an amount of 5.0% w/v. In one preferred embodiment, the aqueous solution of the present invention comprises ethanol as the sole co-solvent. It was found out that when ethanol alone was used to prepare a ready-to-administer parenteral dosage form of diltiazem, comprising ready-to-infuse aqueous solution of diltiazem, the resulting parenteral dosage form was stable at 2-8° C. and at room temperature (25° C.) upon storage for prolonged period of time. Further, it was a surprising finding that the content of impurities in formulation using ethanol was substantially lower as compared to those observed for parenteral dosage forms that are devoid of ethanol or parenteral dosage forms that contain other water miscible/alcoholic co-solvents such as glycerol, propylene glycol, polyethylene glycol 300 (PEG-300), polyethylene glycol 400 (PEG-400). It was indeed surprising to find that while use of ethanol alone resulted in a stable, ready-to-infuse aqueous solution of diltiazem, the use of other water miscible co-solvents, like glycerol, propylene glycol, polyethylene glycol 300 or polyethylene glycol 400, resulted in formation of higher levels of impurities such as desacetyl-diltiazem impurity and total impurities, upon storage. This is presented in FIG. 1, which indicates an increase in total impurities observed for the parenteral dosage form having aqueous solution of diltiazem with cosolvents other than ethanol, like glycerol, glycols. In one such embodiment, when the parenteral dosage form having aqueous solution of diltiazem with 5% w/v ethanol was stored at 2-8° C. for 6 months, the assay of diltiazem was found to remain within the acceptable limits of 95-105% and the content of desacetyl diltiazem impurity which is the major known impurity, was 0.57% (less than 1.0%) and the content of total impurity was 0.6% (less than 1.0%).

The parenteral dosage form and the ready-to-infuse aqueous solution of the present invention further comprise other parentally acceptable excipients. The parentally acceptable excipients that may be used include, but not limited to pH adjusting agents and buffers, osmotic/tonicity adjusting agents, chelating agents, etc. In one preferred embodiment, the dosage form is free of anti-oxidants and preservatives. In preferred embodiment, the dosage form is free of oily excipients or other agents used in formulating topical dosage forms.

The pH of the aqueous solution may be adjusted in the desired range by use of a pH adjusting agent. The pH adjusting agent includes buffering agents known in the pharmaceutical art. The pH adjusting and/or buffering agent that may be used include, but are not limited to citric acid, sodium citrate, sodium hydroxide, hydrochloric acid, sulfuric acid, acetic acid, sodium acetate, tartaric acid, potassium hydroxide and the like and mixtures thereof. In one embodiment the pH may be auto-adjusted in the desired range by the ingredients present in the solution of the present invention. The pH of the solution ranges from about 3 to 5, preferably about 3.5 to 4.5, such as for example 3.6, 3.7, 3.8, 3.9, 4.0, 4.1, 4.2, 4.3 or 4.4, and more preferably from about 3.7 to about 4.1. In one preferred embodiment the ready-to-infuse solution of diltiazem comprises or consists essentially of citric acid or citrate buffer to adjust and maintain the pH in the range of 3.5 to 4.5. The ready-to-infuse aqueous solution of the present invention is iso-osmolar to the parenteral/plasma fluids. The tonicity adjusting agent that may be used may be selected from, but are not limited to, mannitol, dextrose, sucrose, sorbitol, sodium chloride, potassium chloride, calcium chloride, and the like and mixtures thereof. In one preferred embodiment, the aqueous solution is devoid of sodium chloride. The aqueous solution of the present invention may further comprise a chelating agent. The chelating agent that may be used is selected from, but is not limited to, disodium edetate dihydrate, disodium edetate, edetic acid, ethylenediamine tertaacetic acid, diethylenetriamine pentaacetic acid.

In preferred embodiments, the infusion container of the parenteral dosage form of the present invention is a flexible infusion container, made up of a flexible material such as plastic or any other polymeric material. In one or more embodiments, the flexible infusion container may be an infusion bag or pouch or soft bag or film and the like. In another embodiment, the infusion container is a pre-filled syringe. The container may include one or more layers of such materials. Suitably, such materials may include but are not limited to, polyolefin polymers, polyethylene, polypropylene; cyclo olefin polymers, cyclo olefin copolymers, polypropylene based polyolefin polymers; polycarbonates; modified polyolefin-polyethylene polymers or styrene-polyolefin based polymers and block co-polymers thereof.

Particularly, the flexible infusion container is not impermeable in nature and possesses some permeation characteristics and the aqueous solution of diltiazem remains in contact with these materials of the container throughout the shelf life of the dosage form. The container may be single or multiple layered and made up of a suitable material such as plastic or any other polymeric material. Such materials may be selected from, but not limited to, polyolefin polymers-polyethylene, polypropylene; cyclo olefin polymers, cyclo olefin copolymers, polypropylene based polyolefin polymers; modified polyolefin-polyethylene polymers or styrene-polyolefin based polymers and block co-polymers thereof. These plastic materials of the container may further have one or more outer layers which may be made up of polyamide, modified polyolefin, polypropylene, styrene-polyolefin based polymers and block co-polymers thereof and the like. In one specific embodiment, the flexible infusion containers are made up of an outer layer of polyamide 11, a middle tie of modified polyolefin and an inner layer of linear low density polyethylene. This type of containers have a water vapour transmission rate of 2 g (m$^2$·day) when measured at (40° C./90% relative humidity); oxygen transmission rate of 900 ml/(m$^2$·24 hour·atm) when measured at (23° C./0% relative humidity) and carbon dioxide transmission rate of 600 ml/(m$^2$·24 hour·atm) when measured at 23° C./0% relative humidity. Such containers are available commercially and are manufactured by Hosokawa as Polyelite AE-1. In another preferred embodiment, the flexible infusion containers may be made up of a material comprising a polymer of cyclic olefin such as cyclooolefin homopolymer or cycloolefin copolymer or mixture thereof. Specifically, in a particular embodiment, the container comprises an inner layer made up of a cycloolefin polymer, a middle layer made up of linear low density polyethylene polymer and an outer layer made up of low density polyethylene polymer. Such containers are available commercially and are manufactured by Hosokawa as Polyelite EHC film bag. These containers have a water vapour transmission rate of 2 g (m$^2$·day) when measured at (40° C./90% relative humidity); oxygen transmission rate of 570 ml/(m$^2$·24 hour·atm) when measured at (23° C./0% relative humidity) and carbon dioxide transmission rate of 3400 ml/(m$^2$·24 hour·atm) when measured at 23° C./0% relative humidity. In another embodiment, the flexible infusion containers may be made up of an outer layer of polypropylene polymer with styrene-ethylene-butylene (SEB) block copolymer and a middle and inner layer made up of polypropylene based polyolefin polymer with styrene-ethylene butylene block copolymer. Such containers are available commercially and are manufactured by Technoflex. These type of containers have a water vapour transmission rate of 0.62 g (m$^2$·day) when measured at 23° C./60% relative humidity; oxygen permeability of 1110 ml/(m$^2$·24 hour·atm) when measured at 23° C./40% relative humidity and carbon dioxide transmission rate of 5149 ml/(m$^2$·24 hour·atm). Alternatively, the flexible container is made up of multilayer polyolefin film having layers from outside to inside made up of CPET-Tie-PE-Tie-EPC. Such containers are available as M312 and M312A® films by Sealer Air Corporation. These containers have a water vapour transmission rate of 5.0 g (m$^2$·day) when measured at 38° C./100% relative humidity; oxygen transmission rate of 1315 cm$^3$/(m$^2$·24 hour·atm) when measured at 73° F./0% relative humidity and carbon dioxide transmission rate of 3945 cm$^3$/(m$^2$·24 hour·atm).

In one embodiment, the infusion containers may include a Minitulipe® infusion port which is an infusion connector having three assembled parts including a central stopper made up of chlorobutyl rubber (latex free); an upper breakable part and a bottom part, both made up of polycarbonate. In one embodiment, the infusion container contains a delivery port end for insertion of an infusion set cannula/needle. In one embodiment, the infusion container/bag and the delivery port connecting to the infusion needle form a system whereby during administration of the solution to the patient the vacuum created by outgress of solution is accommodated by the elasticity or flexibility of the infusion bag instead of ingress of external non-sterile air. The dosage form can advantageously maintain the sterility of the solution until it reaches the patient.

In one embodiment, the flexible infusion container includes a thermally resealable portion that is fusible in response to thermal energy, and a container body having a sealed empty chamber in fluid communication with the resealable portion for receiving therein the aqueous solution of the present invention. The method of filling the container includes penetrating the resealable portion with an injection member and introducing the aqueous solution of the present invention into the chamber, withdrawing the injection member while engaging the base of the body to substantially prevent axial movement of the body, and applying thermal energy to the resealable portion to thermally fuse the penetrated region thereof. Such systems are elaborated in U.S. Pat. No. 7,992,597, which is incorporated herein by reference.

In another embodiment, the flexible infusion container may include a chamber for receiving aqueous solution of the present invention and a thermoplastic portion in fluid communication with the chamber. The thermoplastic portion defines a penetrable region that is penetrable by a filling member and is heat resealable to hermetically seal an aperture therein by applying laser radiation at a predetermined wavelength and power and in a predetermined time period. Such systems are elaborated in U.S. Pat. No. 7,490,639, which is incorporated herein by reference.

In yet another embodiment, the flexible infusion container include a sealed chamber; a first penetrable septum in fluid communication with the chamber that is formed of an elastic material and is penetrable by a first injection member to fill the first chamber with the aqueous solution of the present invention therethrough; and a second penetrable septum movable between first and second positions. In the first position, at least a portion of the second septum is spaced away from the first septum to allow the injection member to penetrate the first septum and aseptically or sterile fill the chamber with the aqueous solution of the present invention therethrough. In the second position, the portion of the second septum overlies and seals a resulting injection aperture in the first septum after withdrawal of the first injection member therefrom, and is penetrable by a second injection member to penetrate the first and second septums and withdraw the filled aqueous solution of the present invention from the chamber and through the second injection member. Such systems are elaborated in United States patent application number US20130333796, which is incorporated herein by reference.

In one embodiment, the infusion container is rigid and it is made up of material such as glass. Such infusion containers include infusion vials, infusion bottles, or pre-filled syringes. However, in preferred embodiments, the container does not have material that contains borate or boron.

In another embodiment of the present invention, the container may be a pre-filled syringe. The pre-filled syringe may be made up of a material having at least one non-glass component. The barrel of the pre-filled syringe can preferably be made up of appropriate plastic or polymeric material. In a preferred aspect, the syringe comprises a barrel made up of cyclic olefin polymer, cyclic olefin copolymer, polypropylene, polycarbonate and the like. The syringe may further comprise an elastomeric tip cap, made up of material such as chloro-butyl formulation. The syringe may comprise a plunger stopper made up of rubber material such as bromo-butyl rubber.

In one embodiment, the container may be further packaged in a secondary packaging. The secondary packaging may comprise a second container such as a pouch or overwrap or film or carton. The secondary packaging may further comprise an oxygen scavenger. In one embodiment, the secondary packaging is designed to protect the solution of diltiazem from light. In preferred embodiments, the secondary packaging pouch or film or overwrap or carton is made up of a suitable light protective material such as aluminum. Non limiting example of the material constituting secondary packaging or secondary containers include, aluminum, various polymers and copolymers like polyamide, ethylenevinyl alcohol copolymer etc. Aluminum based containers are preferred and include aluminium pouches, aluminium plated films, aluminium foils, aluminum laminate films, composite aluminum films co-extruded with other polymers like polyethylene, polypropylene, EVA, EMA, EAA etc. In one preferred embodiment, the secondary container is an overwrap pouch made up of composite polymer aluminium film having PET, Nylon-6, aluminium foil, and CPP (polypropylene/ethylene block copolymer) from outside to inside, the layers being either co-extruded and/or fixed using an adhesive with the other layer. In another preferred embodiment, the secondary container is an overwrap pouch made up of PET/NY/Aluminum/Oxygen absorbing layer/Polyethylene. In another preferred embodiment, the second container is an overwrap pouch made up of PET/NY/Aluminum/Oxygen absorbing layer/Polypropylene. In another preferred embodiment, the second container is an overwrap pouch made up of PET/NY/AL/OA/CPP. In some preferred embodiments, the dosage form may further comprise an oxygen scavenger, which may be placed in between the infusion container and the second overwrap container or in some embodiments, the overwrap pouch may have a layer of oxygen absorbing material which acts as an oxygen scavenger, such as fused silica bags or iron containing adsorbents like iron oxide and the like. The oxygen scavenger or oxygen scavenging layer material may be a suitable material capable of quickly absorbing oxygen and having good oxygen absorbing capacity and heat resistance. Non-limiting example of such oxygen scavenging materials include iron, silica, charcoal etc. Preferably the oxygen scavenging material is iron based material. In one embodiment, the oxygen scavenger may be an iron based self-reacting type or iron based water dependent type oxygen scavenger/absorber (such as those marketed under the brand of AGELESS®). In one embodiment, the space between the infusion container and secondary overwrap container or pouch is filled with an inert gas such as nitrogen or argon.

The parenteral dosage form of the present invention is sterile. The term "sterile" or 'sterilized' as used in the context of the invention, means that the aqueous solution has been brought to a state of sterility and has not been subsequently exposed to microbiological contamination, i.e. the sterility of the solution present in the container has not been compromised. The solution complies with the sterility requirements of the standard Pharmacopoeias like United States Pharmacopoeias (USP). Sterilization may be achieved by suitable techniques such as filtration sterilization, radiation sterilization and the like. In one preferred embodiment, the parenteral dosage form of the present invention is subjected to sterilization by membrane filtration of the aqueous solution. A 0.2 micron membrane capsule filter may be used.

In one embodiment, the present invention provides a parenteral dosage form comprising a) a ready-to-infuse, stable aqueous solution consisting of diltiazem or its pharmaceutically acceptable salt, citric acid to provide a pH in the range of 3 to 5 and ethanol, and b) an infusion container filled with said aqueous solution, wherein the infusion container is a flexible infusion bag, and it is overwrapped by an aluminium pouch. In one specific embodiment, the parenteral dosage form further comprises an oxygen scavenger.

In the context of this specification "comprising" is to be interpreted as "including". Aspects of the invention comprising certain elements are also intended to extend to alternative embodiments "consisting" or "consisting essentially" of the relevant elements.

Where technically appropriate, embodiments of the invention may be combined.

Embodiments are described herein as comprising certain features/elements. The disclosure also extends to separate embodiments consisting or consisting essentially of said features/elements.

Any embodiments specifically and explicitly recited herein may form the basis of a disclaimer either alone or in combination with one or more further embodiments.

Hereinafter, the invention will be more specifically described by way of Examples. The examples are not intended to limit the scope of the invention and are merely used as illustrations.

Example I-IV

The following examples I to IV exemplify parenteral dosage forms according to preferred embodiments of the present invention.

TABLE 1

Ready-to-infuse aqueous solutions of Diltiazem

| Ingredients | Amount - mg/ml Example number | | | |
|---|---|---|---|---|
| | I | II | III | IV |
| Diltiazem HCl | 1 | 1 | 1 | 1 |
| Ethanol | 50 | 100 | 10 | 50 |
| Sodium citrate | — | — | — | 0.13 |
| Citric Acid | q.s. to pH 3.9 | | | |
| Water for Injection | q.s. to 1 mL | | | |

Procedure: A part of water for injection, maintained at 2-8° C., was taken in a container and ethanol was added and mixed. The pH of the aqueous solution was adjusted in the range of 3.7 to 4.1, particularly 3.9, using citric acid and/or sodium citrate. To this solution, diltiazem hydrochloride was added and dissolved along with stirring. The volume was made up to the desired level using water for injection. The solution so obtained was sterilized by filtration using 0.2 micron membrane capsule filter. 100 ml of the filtered solution having 1 mg/ml diltiazem hydrochloride was filled in a flexible infusion bag and stoppered. The resulting bag was further overwrapped using an aluminum pouch along with an oxygen scavenger and the dosage form was charged for stability study.

The parenteral dosage form comprising ready-to-infuse aqueous solution of diltiazem so obtained (example I) was checked for chemical stability and was found to be stable upon storage at 2-8° C. and at 25° C./40% relative humidity (accelerated storage stability condition). The accelerated stability at 25° C. was tested for 6 months. The assay of diltiazem was within 95-105% upon storage at 2-8° C. for at least 12 months and upon storage at 25° C. for 6 months. The solution of example I when stored at 2-8° C., the content of desacetyl diltiazem was 0.57% (less than 1.0%) and the total impurities was 0.6% (less than 1.0%) at 6 month and at 12 month, the content of desacetyl diltiazem was 1.199% (less than 2.0%) and the total impurities was 1.224% (less than 2.0%).

Comparative Examples A to E

The following comparative examples A to E exemplify comparative parenteral dosage forms:

TABLE 2

Composition details of comparative examples - A, B, C, D & E

| Ingredients | COMPARATIVE EXAMPLES (mg/ml) | | | | | Example (V) as per present Invention (mg/ml) |
|---|---|---|---|---|---|---|
| | A | B | C | D | E | |
| Diltiazem Hydrochloride | 1* | | | | | 1* |
| Glycerol | — | 500 | — | — | — | — |
| Polyethylene Glycol-300 | — | — | 500 | — | — | — |
| Polyethylene Glycol-400 | — | — | — | 500 | — | — |
| Propylene Glycol | — | — | — | — | 500 | — |
| Ethanol | — | — | — | — | — | 500 |
| pH | 3.5 to 5.5 | | | | | 5.0 |
| Water for Injection | q.s. to 1 mL | | | | | q.s. to 1 mL |

*= amount in mg/ml

The aqueous solutions A to E were (100 ml each) were filled in separate infusion containers and tested under stress stability conditions (40° C./25% Relative Humidity) and the content of total impurities and desacetyl diltiazem impurity were estimated and the levels were compared with that of formulation according to the present invention that have ethanol, under same conditions.

It was observed that in case of the comparative formulations A to E, (which either have no co-solvent (A) or have co-solvents other than ethanol (B to E), there occurs formation of significantly higher amounts of total impurities as compared to those observed for formulation having ethanol as per present invention (example V) Similarly, there occurs formation of significantly higher amounts of desacetyl diltiazem impurity as compared to those observed for formulation having ethanol as per present invention. The result for increase in total impurities for various batches upon storage at 40° C./25% relative humidity for 3 days is presented in FIG. 1.

The invention claimed is:

1. A parenteral dosage form comprising:
   a. a ready-to-infuse, stable aqueous solution comprising diltiazem or its pharmaceutically acceptable salt, a pH adjusting agent to provide a pH in the range of 3 to 5, and ethanol,
   b. an infusion container filled with from about 50 ml to about 500 ml of the aqueous solution,
   wherein the aqueous solution is stable at room temperature for at least 6 months or 2°-8° C. for at least 6 months, or both, and has less than 2% of desacetyl diltiazem impurity,
   wherein the aqueous solution does not contain glycerol and glycols, and
   wherein said dosage form is for parenteral administration.

2. The parenteral dosage form according to claim 1, wherein the diltiazem or its pharmaceutically acceptable salt is present at a concentration of about 0.4 mg/ml to about 1.0 mg/ml.

3. The parenteral dosage form according to claim 1, wherein ethanol is present at a concentration ranging from about 1.0% w/v to about 10.0% w/v.

4. The parenteral dosage form according to claim 1, wherein the infusion container is made of plastic and is flexible.

5. The parenteral dosage form according to claim 1, wherein the aqueous solution has total impurity of less than 2% when stored at room temperature for at least 6 months.

6. The parenteral dosage form according to claim 1, wherein the aqueous solution has total impurity of less than 2% when stored at 2° C.-8° C. for at least 6 months.

7. A parenteral dosage form comprising:
   a. a ready-to-infuse, stable aqueous solution consisting essentially of diltiazem or its pharmaceutically acceptable salt, a pH adjusting agent to provide a pH in the range of 3 to 5, and ethanol,
   b. an infusion container filled with from about 50 ml to about 500 ml of the aqueous solution,
   wherein the aqueous solution is stable at room temperature for at least 6 months or 2°-8° C. for at least 6 months, or both, and has less than 2% of desacetyl diltiazem impurity, and
   wherein said dosage form is for parenteral administration.

8. The parenteral dosage form according to claim 7, wherein the diltiazem or its pharmaceutically acceptable salt is present at a concentration of about 0.4 mg/ml to about 1.0 mg/ml.

9. The parenteral dosage form according to claim 7, wherein ethanol is present at a concentration ranging from about 1.0% w/v to about 10.0% w/v.

10. The parenteral dosage form according to claim 7, wherein the infusion container is made of plastic and is flexible.

11. The parenteral dosage form according to claim 7, wherein the aqueous solution has total impurity of less than 2% when stored at room temperature for at least 6 months.

12. The parenteral dosage form according to claim 7, wherein the aqueous solution has total impurity of less than 2% when stored at 2° C.-8° C. for at least 6 months.

13. A parenteral dosage form comprising:
   a. a ready-to-infuse, stable aqueous solution consisting of (a) diltiazem or its pharmaceutically acceptable salt, (b) citric acid to provide a pH in the range of 3 to 5, (c) ethanol, and (d) optionally, sodium citrate,
   b. an infusion container filled with from about 50 ml to about 500 ml of the aqueous solution,
   wherein the aqueous solution is stable at room temperature for at least 6 months or 2°-8° C. for at least 6 months, or both, and has less than 2% of desacetyl diltiazem impurity,
   wherein the aqueous solution does not contain glycerol and glycols, and
   wherein the dosage form is for parenteral administration.

* * * * *